United States Patent
King et al.

(10) Patent No.: US 9,611,351 B2
(45) Date of Patent: Apr. 4, 2017

(54) AMINE POLYETHER POLYOLS AND POLYURETHANE FOAM COMPOSITIONS MADE FROM CYCLIC AMINE COMPOUNDS

(71) Applicant: Dow Global Technologies LLC, Midland, MI (US)

(72) Inventors: Stephen W. King, League City, TX (US); Esther Quintanilla, Zurich (CH); Jean-Paul Massy, Destelbergen (BE); David H. Bank, Midland, MI (US); Erin B. Vogel, Midland, MI (US); Francois Rene Morgan Graf, Wangen (CH); Adrian J. Birch, Kempraten-Jona (CH)

(73) Assignee: DOW GLOBAL TECHNOLOGIES LLC., Midland, MI (US)

( * ) Notice: Subject to any disclaimer, the term of this patent is extended or adjusted under 35 U.S.C. 154(b) by 132 days.

(21) Appl. No.: 14/369,626

(22) PCT Filed: Dec. 28, 2012

(86) PCT No.: PCT/US2012/072032
§ 371 (c)(1),
(2) Date: Jun. 27, 2014

(87) PCT Pub. No.: WO2013/102053
PCT Pub. Date: Jul. 4, 2013

(65) Prior Publication Data
US 2014/0357750 A1    Dec. 4, 2014

Related U.S. Application Data

(60) Provisional application No. 61/581,323, filed on Dec. 29, 2011, provisional application No. 61/717,901, filed on Oct. 24, 2012.

(51) Int. Cl.
*C08G 18/32* (2006.01)
*C07D 295/13* (2006.01)
*C08G 18/72* (2006.01)

(52) U.S. Cl.
CPC ....... *C08G 18/3246* (2013.01); *C07D 295/13* (2013.01); *C08G 18/72* (2013.01)

(58) Field of Classification Search
CPC ... C08G 18/3246; C08G 18/72; C07D 295/13
See application file for complete search history.

(56) References Cited

U.S. PATENT DOCUMENTS

| 4,568,746 A | 2/1986 | Cowherd, III |
| 4,863,890 A | 9/1989 | Köll |
| 4,973,692 A | 11/1990 | Burgess et al. |
| 4,977,266 A | 12/1990 | Burgess et al. |
| 4,992,587 A | 2/1991 | Köll |
| 5,196,588 A | 3/1993 | Burgess et al. |
| 5,256,786 A | 10/1993 | Bowman et al. |
| 5,362,700 A * | 11/1994 | Doumaux, Jr. .......... B01J 27/18 502/208 |
| 5,410,086 A | 4/1995 | Burgess |
| 6,307,102 B1 | 10/2001 | Tokumoto et al. |
| 6,465,601 B1 | 10/2002 | Wiesendanger et al. |
| 6,534,441 B1 | 3/2003 | Bartley et al. |
| 7,053,247 B2 | 5/2006 | Lif et al. |
| 8,187,997 B2 | 5/2012 | King et al. |
| 8,188,318 B2 | 5/2012 | Petraitis et al. |
| 8,293,676 B2 | 10/2012 | King et al. |
| 8,367,870 B2 | 2/2013 | Burdeniuc et al. |
| 8,383,861 B2 | 2/2013 | Do et al. |
| 2003/0032553 A1 | 2/2003 | Wendel et al. |
| 2008/0004362 A1* | 1/2008 | Masuda ................ C07C 217/08 521/184 |
| 2008/0090922 A1 | 4/2008 | Vedage et al. |
| 2008/0132725 A1 | 6/2008 | Melder et al. |
| 2010/0087683 A1 | 4/2010 | Cook et al. |
| 2010/0094007 A1 | 4/2010 | King et al. |
| 2010/0216361 A1 | 8/2010 | Bruchmann et al. |
| 2010/0305228 A1 | 12/2010 | Gossner et al. |
| 2010/0324261 A1 | 12/2010 | Muelhaupt et al. |
| 2015/0005404 A1 | 1/2015 | Latham et al. |
| 2015/0011762 A1 | 1/2015 | King |

FOREIGN PATENT DOCUMENTS

| EP | 0 412 611 | 2/1991 |
| EP | 0 414 574 | 2/1991 |
| EP | 0 737 669 | 10/1996 |
| GB | 1508460 | 4/1978 |
| GB | 1551127 | 8/1979 |
| WO | WO 96/38226 | 12/1996 |
| WO | 2004/060956 A1 | 7/2004 |
| WO | 2010008675 A1 | 1/2010 |
| WO | WO 2010/042157 | 4/2010 |
| WO | 2012006548 A1 | 1/2012 |
| WO | WO 2013/101345 | 7/2013 |
| WO | WO 2013/102097 | 7/2013 |

OTHER PUBLICATIONS

Bazzicalupi, C., et al., (1998) *Reinforced piperazine rings containing polyamines: metal complex equilibria and structural studies*, Inorganica Chimica Acta 268: 63-68.

Marchand, A.P., et al., (2004) *Synthesis and Electrospray Ionization Mass Spectrometric Evaluation of the Metal Cation Complexation Behavior of Cage-Annulated Azacrown Ethers*, Heterocycles 62: 279-296.

* cited by examiner

*Primary Examiner* — John Cooney

(74) *Attorney, Agent, or Firm* — Kagan Binder, PLLC

(57) ABSTRACT

The present invention describes cyclic amine compounds useful for catalysts for polyurethane form-forming compositions, as well as amine alkoxylates and amine polyether polyols formed form the cyclic amines. The cyclic amine compounds of the invention provide distinct benefits for reaction compositions, methods, and polyurethane foams based on their desirable physical and catalytic properties.

16 Claims, 2 Drawing Sheets

AMINE POLYETHER POLYOLS AND POLYURETHANE FOAM COMPOSITIONS MADE FROM CYCLIC AMINE COMPOUNDS

This application claims benefit from International Application No. PCT/US2012/072032 which was filed on Dec. 28, 2012, which in turn claims priority to U.S. Provisional Patent Application Ser. No. 61/717,901 filed Oct. 24, 2012; and U.S. Provisional Patent Application Ser. No. 61/581,323 filed Dec. 29, 2011, the disclosures of which are incorporated herein by reference.

PRIORITY CLAIM

This application claims the benefit of U.S. Provisional Application Ser. No. 61/581,323, filed Dec. 29, 2011, entitled "FORMATION OF HIGHER MOLECULAR WEIGHT CYCLIC POLYAMINE COMPOUNDS FROM CYCLIC POLYAMINE COMPOUNDS" and U.S. Provisional Application Ser. No. 61/717,901, filed Oct. 24, 2012, entitled "AMINE POLYETHER POLYOLS AND POLYURETHANE FOAM COMPOSITIONS MADE FROM CYCLIC AMINE COMPOUNDS", which applications are incorporated herein by reference in their entirety.

FIELD

The present invention pertains to cyclic amines, amine alkoxylates derived from cyclic amines, amine polyether polyols derived from the cyclic amines, and polyurethane foams prepared from the cyclic amines, amine alkoxylates, or amine polyether polyols.

BACKGROUND

Polyurethane foams typically are produced by the reaction of polyols with isocyanates in the presence of water acting as blowing agent. The reaction leading to polyurethane foam formation reaction generally consists of the urethane reaction (gelling) and urea reaction (blowing), which is associated with carbon dioxide ($CO_2$) production. Catalysts as well as other auxiliary agents, such as cross-linkers, chain extenders, surfactants, stabilizers, and antioxidants, are often included in the composition with the polyol and isocyanate components. Catalysts can play a key role in ensuring desirable foam properties by controlling and balancing the gelling and blowing reactions during foam production. Catalysts can also have an effect on moldability and cure speed of the foam.

Tertiary amines and organometallic salts have been used in the art as catalysts for polyurethane foams. However, commonly used tertiary amine catalysts give rise to several problems, particularly in flexible, semi-rigid and rigid foam applications. Freshly prepared foams using these catalysts often have the typical odor of the amines and give rise to increased fogging due to emission of volatile products.

The presence, or formation, of tertiary amine catalyst vapors in polyurethane products are detrimental to vinyl films or polycarbonate sheets exposed thereto. Specifically, the tertiary amine catalysts present in polyurethane foams have been linked to staining of vinyl films and the degradation of polycarbonate sheets. These PVC staining and polycarbonate decomposition problems are especially prevalent in environments wherein elevated temperatures exist for long periods of time, such as in automobile interiors.

The inventors of the current application have understood that many difficulties exist in producing desirable polyurethane foam products for consumer and industrial applications and that the preparation and identification of amine catalysts desirable for polyurethane foams is still a challenging area. For example, while some catalysts (e.g., see U.S. Pat. No. 4,517,313) are stated to reduce odor and vinyl staining relative to the use of standard triethylenediamine catalysts, they unfortunately provide weaker catalytic activity, and are not up to the standards of conventional catalysts. It is challenging to alter the chemical structure of the amine catalyst without adversely affecting its catalytic activity. In some cases catalysts need to be used at high levels in the polyurethane formulation to compensate for their lack of catalytic activity or mobility during the reactions.

Another issue relates to the stability of compositions, including foam-forming components. Pre-reacted components in a composition may exhibit a tendency to pre-gel or have poor storage stability. Yet another issue is that some catalysts that promote rapid gelling lead to foam processing and foam properties problems. For example, tear strength and elongation at break can be detrimentally affected due to a high level of crosslinking. Further, some catalysts, when subjected to elevated temperatures as are commonly encountered in automobile interiors, migrate within a foam.

The current application provides compounds, compositions, and methods for forming polyurethane foams based on the use of cyclic amine compounds, amine alkoxylates derived from cyclic amines, or amine polyether polyols derived from the cyclic amines.

SUMMARY

The present invention provides compositions, for amine alkoxylates, amine polyether polyols, and polyurethane foams including or derived from cyclic amine compounds. The invention also provides a method for preparing amine alkoxylates, amine polyether polyols, and polyurethane foams using the cyclic amine compounds.

The compositions, amine alkoxylates, amine polyether polyols, and polyurethane foams are prepared using cyclic amines of Formula I:

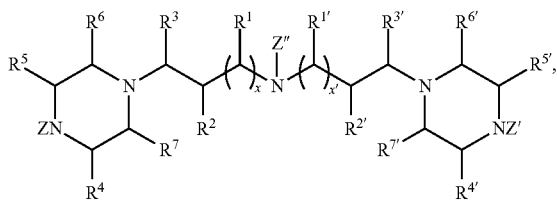

or of Formula II

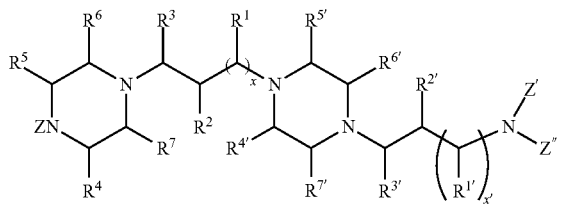

In Formula I and II, $R^1$-$R^7$ and $R^{1'}$-$R^{7'}$ are independently selected from the group consisting of hydrogen and hydrocarbyl groups; x and x' are independently 0 (a covalent bond) or an integer in the range of 1-10, and if x or x' is greater than 1, then $R^1$ and $R^{1'}$ are the same or different; and Z, Z', and Z'' are independently selected from the group consisting of hydrogen and —$CH_2CH_2OH$, —$CH_2CH(CH_3)OH$, —$CH(CH_3)CH_2OH$, —$CH_2CH(CH_2CH_3)OH$, or —$CH(CH_2CH_3)CH_2OH$. Exemplary compounds of Formula I or II have x and x' as 0 (a covalent bond) or 1; have $R^1$-$R^7$ and $R^{1'}$-$R^{7'}$ as hydrogen; and have Z, Z', and Z'' as hydrogen —$CH_2CH_2OH$, —$CH_2CH(CH_3)OH$, —$CH(CH_3)CH_2OH$, —$CH_2CH(CH_2CH_3)OH$, —$CH(CH_2CH_3)CH_2OH$, or mixtures thereof. Included as chemical species in the compounds of Formula I and II are the cyclic amines bis(2-piperazin-1-ylethyl)amine ("BPEA"), (3-(piperazin-1-yl)propyl)amine, bis(4-(piperazin-1-yl)butyl)amine, bis(5-(piperazin-1-yl)pentyl)amine, bis(6-(piperazin-1-yl)hexyl)amine, bis(1-(piperazin-1-yl)propan-2-yl)amine, and bis(2-(piperazin-1-yl)propyl)amine, 2-(4-(2-(piperazin-1-yl)ethyl)piperazin-1-yl)ethanamine, 3-(4-(3-(piperazin-1-yl)propyl)piperazin-1-yl)propan-1-amine, 4-(4-(4-(piperazin-1-yl)butyl)piperazin-1-yl)butan-1-amine, 5-(4-(5-(piperazin-1-yl)pentyl)piperazin-1-yl)pentan-1-amine, 6-(4-(6-(piperazin-1-yl)hexyl)piperazin-1-yl)hexan-1-amine, 1-(4-(1-(piperazin-1-yl)propan-2-yl)piperazin-1-yl)propan-2-amine, and 2-(4-(2-(piperazin-1-yl)propyl)piperazin-1-yl)propan-1-amine and the amine alkoxylates, 2,2'-(4,4'-(((2-hydroxyethyl)azanediyl)bis(ethane-2,1-diyl))bis(piperazine-4,1-diyl))diethanol, 1,1'-(4,4'-(((2-hydroxypropyl)azanediyl)bis(ethane-2,1-diyl))bis(piperazine-4,1-diyl))bis(propan-2-ol), and 1,1'-(4,4'-(((2-hydroxybutyl)azanediyl)bis(ethane-2,1-diyl))bis(piperazine-4,1-diyl))bis(butan-2-ol).

Compounds of Formulas I and II provide significant advantages in the areas of cyclic amines, and amine alkoxylates prepared from said cyclic amines, for use to make polyurethane foams. These compounds as represented by BPEA have desirable physical and catalytic properties for the production of polyurethane foams.

Compounds of Formulas I and II have one or more of the following properties: (a) liquid at room temperature, (b) a low volatile organic compound (VOC) profile (boiling point >250° C. measured at a standard atmospheric pressure) (c) desirable viscosity; (d) good color; (e) no undesirable odor; and (f) desirable catalytic activity. Use of these compounds can provide distinct benefits for foam-forming compositions, methods for making foams, and polyurethane foams per se.

The liquid and viscosity properties of the cyclic amine compound of Formula I or II can ensure better mixing in the foam-forming compositions, and lend to easier handling as compared to more volatile amines or amines that are in solid form. For example, due to both the exothermic nature of the foam-forming reactions and the elevated temperatures for reaction, many known amine catalysts which are volatile cause an odorous release which can be undesirable. Further, the viscosity allows for better molecular mobility which can lead to a more thorough distribution of the compound with enhanced foam-forming reactions which ultimately provides a foam with improved properties. Furthermore, the molecular structure of the cyclic amines and amine alkoxylates is sterically favorable facilitating access to the reactants to promote desired reactions.

As another benefit, the cyclic amine and cyclic amine alkoxylates of Formula I or II have good color and no undesirable odor. These desirable properties can carry over into products made from the cyclic amine or cyclic amine alkoxylate, such as amine polyether polyols, and polyurethane foams. For example, polyurethane foams with a good color may be colorless or substantially colorless, and may be used to make articles that are resistant to staining, etc., and that have higher consumer value. Polyurethane foam products that do not have any objectionable odor also have higher consumer value.

The cyclic amine and amine alkoxylates of Formula I or II also provide good catalytic activity. For example, studies associated with the current invention showed that inclusion of a cyclic amine compound of Formula I or II provided very good catalytic activity by catalyzing the blowing reaction during polyurethane foam generation.

In one aspect, the invention provides a composition comprising a reaction product derived from reactants comprising (a) a cyclic amine of Formula I or II and (b) a polyol-generating monomer; or a reaction composition having reactants comprising (a) a cyclic amine of Formula I or II and (b) a polyol-generating monomer. The groups $R^1$-$R^7$, $R^{1'}$-$R^{7'}$, Z, Z', and Z" are as described herein. Exemplary polyol-generating monomers include epoxides, such as ethylene oxide, propylene oxide, or butylene oxide. Haloalcohols can also be used as polyol-generating monomers. The reaction product of (a) and (b) can be described as an amine polyether polyol.

In a related aspect, the invention provides a method for preparing an amine polyether polyol comprising a step of reacting a cyclic amine of Formula I or II as described herein with a polyol-generating monomer.

In another aspect, the invention provides an amine polyether polyol of Formula III:

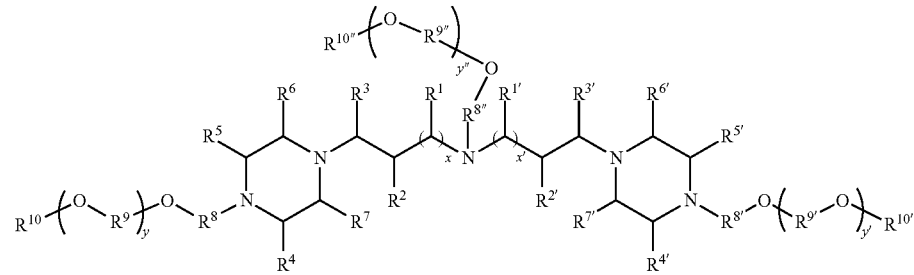

or of Formula IV:

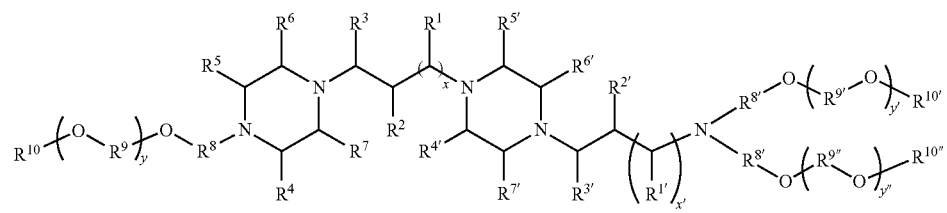

In Formula III or IV, $R^1$-$R^7$, $R^{10}$, $R^{1'}$-$R^{7'}$, $R^{10'}$ and $R^{10''}$ are independently selected from the group consisting of hydrogen and hydrocarbyl groups; x and x' are independently 0 (a covalent bond) or an integer in the range of 1-10, and if x or x' is greater than 1, then $R^1$ and $R^{1'}$ are the same or different; $R^8R^{8'}$, $R^{8''}$, $R^9$, $R^{9'}$, and $R^{9''}$ are independently selected from —CH$_2$CH$_2$—, —CH$_2$CH(CH$_3$)—, —CH(CH$_3$)CH$_2$—, —CH$_2$CH(CH$_2$CH$_3$)—, and —CH(CH$_2$CH$_3$)CH$_2$—; and y, y', and y'' are 0 or an integer in the range of 1 to 250, provided the sum of y, y', and y'' is 1 or greater.

The amine polyether polyol can be used as a reactant, a catalyst, or both, in a composition. If the amine polyether polyol has both reactant and catalytic properties, the amine functionality of the amine polyether polyol can promote reaction catalysis, and the hydroxyl functionalities can be reacted in a bonding process, such as in crosslinking where the amine polyether polyol reacts with a polyisocyanate and becomes incorporated into a polymeric network.

In another aspect, the invention provides a polyurethane foam derived from a composition comprising, or a composition per se comprising: (a) a cyclic amine of Formula I or II, (b) a polyol, and (c) a polyisocyanate. The groups of R, $R^1$-$R^7$, $R^{1'}$-$R^{7'}$, Z, Z', and Z'' of Formula I or II are as described herein.

In a related aspect, the invention provides a polyurethane foam derived from a composition comprising, or a composition per se comprising: (a) an amine polyether polyol of Formula III or IV, (b) optionally a polyol, and (c) a polyisocyanate. The groups of, $R^1$-$R^{10}$, $R^{1'}$-$R^{10'}$, and $R^{8''}$-$R^{10''}$ of Formula III or IV are as described herein.

In a related aspect, the invention provides a method for preparing a polyurethane foam comprising a step of reacting a polyol and a polyisocyanate in the presence of a cyclic amine or amine alkoxylate compound of Formula I or II; or a step of reacting an amine polyether polyol of Formula III or IV with a polyisocyanate, optionally in the presence of a polyol.

Polyurethane foams, including those that are flexible or rigid, formed using the cyclic amine or amine alkoxylate compound of Formula I or II or the amine polyether polyol of Formula III or IV can be used for a variety of applications. Such applications include use in commercial and domestic furniture and bedding; commercial and personal vehicles, such as in seating and interior panels; refrigerators and freezers; construction materials, such as in residential or commercial buildings; garments, clothing, and footwear; packaging materials; as well as electronics and industrial machinery, among others.

DETAILED DESCRIPTION

Figure 1:
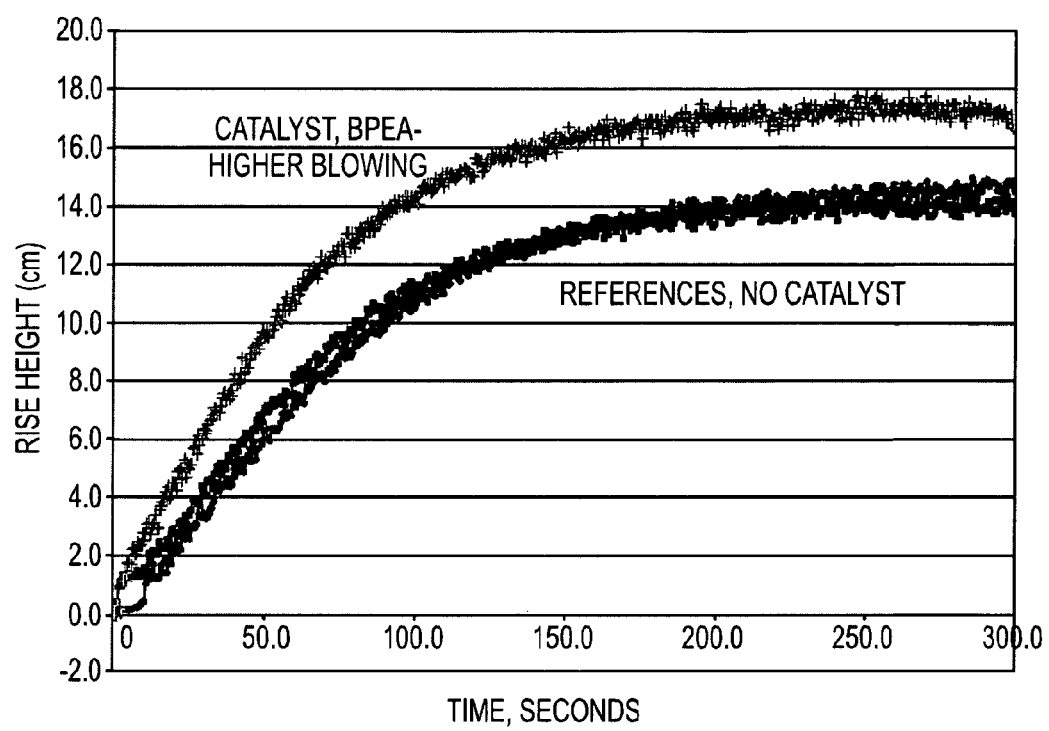
FIG. 1 is a graph showing the increase in height of polyurethane foam compositions over time.

Reference will now be made in detail to representative embodiments of the invention. While the invention will be described in conjunction with the enumerated embodiments, it will be understood that they are not intended to limit the invention to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods, materials, and compositions described.

Unless defined otherwise herein, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

In some aspects, polyurethane foams of the invention can be prepared using cyclic amines or amine alkoxylates of Formula I:

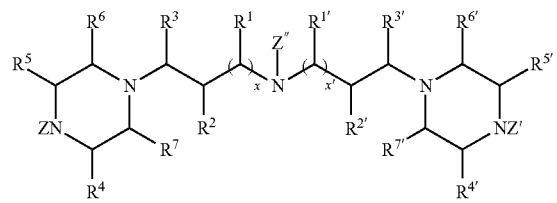

or of Formula II

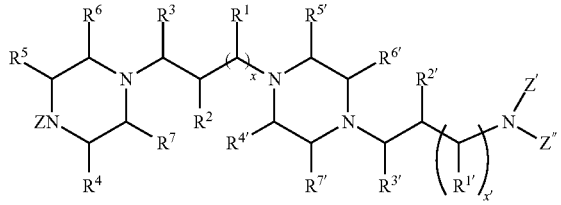

In Formula I or II, $R^1$-$R^7$ and $R^{1'}$-$R^{7'}$ are independently selected from the group consisting of hydrogen and hydrocarbyl groups; x and x' are independently 0 (a covalent bond) or an integer in the range of 1-10, and if x or x' is greater than 1, then $R^1$ and $R^{1'}$ are the same or different; and Z, Z', and Z'' are independently selected from the group consisting of hydrogen and —CH$_2$CH$_2$OH, —CH$_2$CH(CH$_3$)OH, —CH(CH$_3$)CH$_2$OH, —CH$_2$CH(CH$_2$CH$_3$)OH, or —CH(CH$_2$CH$_3$)CH$_2$OH.

Hydrocarbyl groups as referred to herein are substituted or unsubstituted, linear, branched, or cyclic hydrocarbyl groups, such as alkyl, aryl, aralkyl, or the like; a monovalent moiety including one or more heteroatoms; polyether chains comprising one or more oxyalkylene repeating units such as —$R^{11}$O—, wherein $R^{11}$ is often alkylene of 2 to 4 carbon atoms; other oligomeric or polymer chains of at least 2 repeating units. Any of $R^1$-$R^7$ and $R^{1'}$-$R^{7'}$ can be independently selected from hydrocarbyl groups, such as those described herein. In more specific embodiments, $R^1$-$R^7$ and $R^{1'}$-$R^{7'}$ are H, or a straight, branched, or cyclic hydrocarbyl group such as alkyl of 1 to 10 carbon atoms, preferably 1 to 3 carbon atoms. In even more specific embodiments all of $R^1$-$R^7$ and $R^{1'}$-$R^{7'}$ are H.

The values of x and x' in the practice of the invention are 0 or an integer in the range of from 1 to 10, such as in the range of from 2 to 5, or in the range of from 2 to 3, and most preferably 0 or 1.

Exemplary compounds of Formula I or II have x and x' as 0 (a covalent bond); have $R^1$-$R^7$ and $R^{1'}$-$R^{7'}$ as hydrogen; and have Z, Z', and Z" as hydrogen, —$CH_2CH_2OH$, —$CH_2CH(CH_3)OH$, —$CH(CH_3)CH_2OH$, —$CH_2CH(CH_2CH_3)OH$, or —$CH(CH_2CH_3)CH_2OH$.

Examples of cyclic amines of Formula I include bis(2-(piperazin-1-yl)ethyl)amine (BPEA), bis(3-(piperazin-1-yl)propyl)amine, bis(4-(piperazin-1-yl)butyl)amine, bis(5-(piperazin-1-yl)pentyl)amine, bis(6-(piperazin-1-yl)hexyl)amine, bis(1-(piperazin-1-yl)propan-2-yl)amine, bis(2-(piperazin-1-yl)propyl)amine. Examples of cyclic amines of Formula II include 2-(4-(2-(piperazin-1-yl)ethyl)piperazin-1-yl)ethanamine, 3-(4-(3-(piperazin-1-yl)propyl)piperazin-1-yl)propan-1-amine, 4-(4-(4-(piperazin-1-yl)butyl)piperazin-1-yl)butan-1-amine, 5-(4-(5-(piperazin-1-yl)pentyl)piperazin-1-yl)pentan-1-amine, 6-(4-(6-(piperazin-1-yl)hexyl)piperazin-1-yl)hexan-1-amine, 1-(4-(1-(piperazin-1-yl)propan-2-yl)piperazin-1-yl)propan-2-amine, and 2-(4-(2-(piperazin-1-yl)propyl)piperazin-1-yl)propan-1-amine.

Cyclic amines of the Formulas I and II where Z, Z', and Z" are hydrogen, can be made according to processes described in commonly assigned U.S. Provisional Patent Application Ser. No. 61/581,323 entitled "Formation of Higher Molecular Weight Cyclic Polyamine Compounds From Cyclic Polyamine Compounds," filed Dec. 29, 2011 (King). U.S. 61/581,323 describes processes of transaminating a lower molecular weight cyclic amine compound having at least two amine groups separated from one another by a binary carbon spacing (C2 spacing) in the cyclic ring to produce a higher molecular weight, cyclic amine compound of Formula I or II. In particular, compounds of Formula I or II where Z, Z', and Z" are hydrogen can be prepared using a first or lower molecular weight, cyclic amines such as 2-(piperazin-1-yl)ethanamine (AEP), 3-(piperazin-1-yl)propan-1-amine, 4-(piperazin-1-yl)butan-1-amine, 5-(piperazin-1-yl)pentan-1-amine, 6-(piperazin-1-yl)hexan-1-amine, 1-(piperazin-1-yl)propan-2-amine, or 2-(piperazin-1-yl)propan-1-amine.

As described in WO 2013/101345, compounds of Formula I or II where Z, Z', and Z" are hydrogen can be prepared using a hydrogenation/dehydrogenation catalyst that can catalyze the transamination reaction. In preferred embodiments in which a heterogeneous catalyst incorporates nickel and rhenium, a useful support is an alumina-silica. Such catalysts and methods of making such heterogeneous catalysts on such supports are further described in U.S. Pat. No. 6,534,441. Such catalysts are also further described in United States Published Patent Application Nos. 2010-0137642-A1 (King et al.); 2010-0087682-A1 (King et al.); 2010-0087683-A1, (Cook et al.); 2010-0087684-A1, Do et al.; and 2010-0087681-A1, (Petraitis et al.).

As described in WO 2013/101345, the lower molecular weight cyclic amine to be transaminated can be contacted with the catalyst at any suitable temperature(s) and pressure(s) that promotes the production of the higher molecular weight, cyclic amine of the Formulas I and IL Preferred temperatures are in the range from 100° C. to 220° C., more preferably from 120° C. to 180° C. The pressure is typically in the range from 100 psi to 1500 psi, preferably 200 psi to 1200 psi, more preferably 300 psi to 1000 psi. Pressures in the range of 300 psi to 800 psi are most preferred.

In other aspects the compound of Formula I or II is an amine alkoxylate. For amine alkoxylates of Formula I or II, Z, Z', and Z" are independently selected from —$CH_2CH_2OH$, —$CH_2CH(CH_3)OH$, —$CH(CH_3)CH_2OH$, —$CH_2CH(CH_2CH_3)OH$, or —$CH(CH_2CH_3)CH_2OH$. In some aspects the amine alkoxylates are derived from a haloalcohol with the generic structure X—$CH_2CH_2$—OH, X—$CH_2CH(CH_3)$—OH or X—$CH(CH_3)CH_2OH$ or X—$CH_2CH(CH_2CH_3)OH$ or X—$CH(CH_2CH_3)CH_2OH$ where X is Cl, Br, or I.

An amine alkoxylate compound of Formula I or II wherein Z, Z', and/or Z" is —$CH_2CH_2OH$, —$CH_2CH(CH_3)OH$, —$CH(CH_3)CH_2OH$, —$CH_2CH(CH_2CH_3)OH$, or —$CH(CH_2CH_3)CH_2OH$ can be formed by reacting a compound of Formula I or II wherein Z, Z', and/or Z" is H (e.g., BPEA) with ethylene oxide, propylene oxide, butylene oxide, or a mixture thereof under alkoxylation conditions known to one skilled in the art.

Specific examples of amine alkoxylates of Formula I include 2,2'-(4,4'-(((2-hydroxyethyl)azanediyl)bis(ethane-2,1-diyl))bis(piperazine-4,1-diyl))diethanol, 1,1'-(4,4'-(((2-hydroxypropyl)azanediyl)bis(ethane-2,1-diyl))bis(piperazine-4,1-diyl))bis(propan-2-ol), and, 1,1'-(4,4'-(((2-hydroxybutyl)azanediyl)bis(ethane-2,1-diyl))bis(piperazine-4,1-diyl))bis(butan-2-ol).

Specific examples of amine alkoxylates of Formula II include 2,2'-((2-(4-(2-(4-(2-hydroxyethyl)piperazin-1-yl)ethyl)piperazin-1-yl)ethyl)azanediyl)diethanol, 1,1'-((2-(4-(2-(4-(2-hydroxypropyl)piperazin-1-yl)ethyl)piperazin-1-yl)ethyl)azanediyl)bis(propan-2-ol), and 1,1'((2-(4-(2-(4-(2-hydroxybutyl)piperazin-1-yl)ethyl)piperazin-1-yl)ethyl)azanediyl)bis(butan-2-ol).

Prior to further modification, or use in a polyurethane foam-forming composition, compounds of Formula I or II can be separated (refined) by any method known in the art. Methods for purification or separation include conventional distillation technology using dividing wall columns, membrane separation, melt crystallization, and reactive distillation.

Compounds of Formula I or II can be used in "neat" form, as, for example, a liquid, with no solvent present. For example, bis(2-(piperazin-1-yl)ethyl)amine (BPEA) is a liquid at room temperature (~25° C.), and has a boiling point of (~360° C.). Alternatively, the compounds of Formula I or II can be used along with a solvent, or combination of solvents. Desirably, the solvent is not unduly reactive with the cyclic amine product of Formula I or II. If solvent is present, it may be carried over from the synthesis of the cyclic amine product as referred to herein. Some examples of solvents that could in mixture with the cyclic amine include saturated hydrocarbons such as pentane, hexane, octane, nonan, decane, or the like; aromatic hydrocarbons such as toluene, benzene, xylene, ether, combinations of these, and the like.

In other aspects of the invention, amine polyether polyols are provided, which can be prepared using the cyclic amines or amine alkoxylates of Formulas I or II as starting materials.

The amine polyether polyols are according to Formula III:

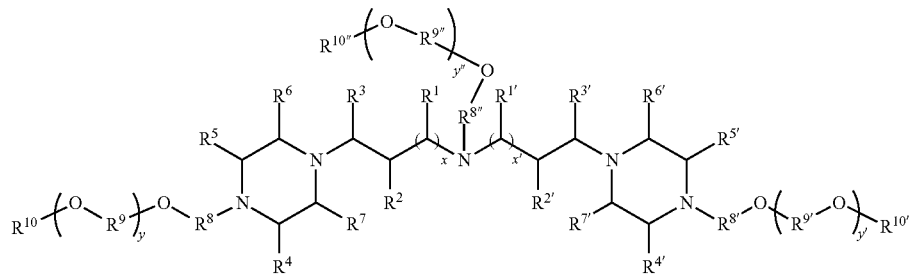

or according to Formula IV:

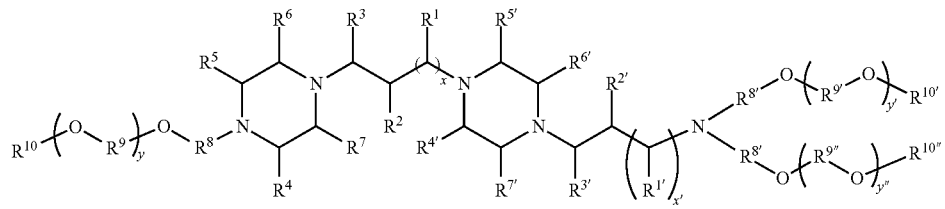

In Formula III and IV, $R^1$-$R^7$, $R^{10}$, $R^{1'}$-$R^{7'}$, $R^{10'}$, and $R^{10''}$ are independently selected from the group consisting of hydrogen and hydrocarbyl groups; x and x' are independently 0 (a covalent bond) or an integer in the range of 1-10, and if x or x' is greater than 1, then re and $R^{1'}$ are the same or different; $R^8$ $R^{8'}$, $R^{8''}$, $R^9$, $R^{9'}$, and $R^{9''}$ are independently selected from —$CH_2CH_2$—, —$CH_2CH(CH_3)$—, —CH($CH_3$)$CH_2$—, —$CH_2CH(CH_2CH_3)$—, —CH($CH_2CH_3$)$CH_2$—; and y, y', and y" are 0 or an integer in the range of 1 to 250, provided the sum of y, y', and y" is 1 or greater.

Compounds of Formula III or IV can be prepared by polymerizing polyol-generating monomers in the presence of a compound of Formula I or II, wherein Z, Z', and/or Z" is —$CH_2CH_2OH$, —$CH_2CH(CH_3)OH$, —CH($CH_3$)$CH_2OH$, —$CH_2CH(CH_2CH_3)OH$, or —CH($CH_2CH_3$)$CH_2OH$.

Exemplary polyol-generating monomers include ethylene oxide, propylene oxide, or butylene oxide which can generate a polyether polyol chain (e.g., —$R^8O(R^9O)R^{10}$) by extending from one or more nitrogen(s) in the piperazinyl ring. Compounds of Formula I or II can be used to initiate the polymerization reaction; optionally polymerization can be carried out in the presence of other initiators or catalysts, such as a strong base like potassium hydroxide or a double metal cyanide catalyst such as zinc hexacyanocobaltate-t-butanol complex.

Other polyol-generating monomers include haloalcohols, such as chloroalcohols, as exemplified by $ClCH_2CH_2$—OH, $ClCH_2CH(CH_3)$—OH, ClCH($CH_3$)$CH_2OH$, $ClCH_2CH(CH_2CH_3)OH$, and ClCH($CH_2CH_3$)$CH_2OH$.

Polyether polyol preparation, such as by propylene oxide polymerization, is well known in the art and has been reviewed by Villa (*Ind. Eng. Chem. Res.* 2007, 46, 5815-5823). Polyether polyol chain length can be controlled by one or more factors, such as the ratio (mol %) of the compounds of Formula I or II to the polyol-generating monomers, the type and amount of catalyst used, and the reaction conditions, including time and temperature. For polymerization, exemplary ranges of a compound of Formula I or II to the polyol-generating monomer (mol:mol) is in the range of about 1:3 to about 1:1500, about 1:30 to about 1:600, or more specifically about 1:75 to about 1:300.

In exemplary embodiments, in Formula III or IV, and y, y', and y" are independently 0 or integers in the range of 1 to about 250, about 10 to about 100, or more specifically about 25 to about 75, provided that the sum of and y, y', and y" is 1 or greater. Amine polyether polyols of Formula III or IV can also be described in terms of hydroxyl number. In exemplary embodiments, compounds of Formula III or IV have a hydroxyl number in the range of about 401.6 mg/g to about 24 mg/g, or more specifically about 250 mg/g to 50 mg/g.

Amine polyether polyols of Formula III or IV can also be described in terms of the molecular weight of the entire compound or a portion(s) of the compound, such as the one more polyol arm(s) extending from the piperazinyl ring(s). Exemplary amine polyether polyols compounds of Formula III or IV have a molecular weight in the range of about 296 Da to about 8000 Da, about 420 Da to about 7000 Da, about 750 Da to about 6000 Da, or about 1000 Da to about 5000 Da. The one or more polyol arm(s) extending from piperazinyl ring(s) may have a combined molecular weight in the range of about 45 Da to about 7750 Da, about 300 Da to about 6500 Da, or more specifically about 500 Da to about 5500 Da.

Compounds of Formula III or IV can optionally be described in terms of their physical properties. For example, amine polyether polyol compounds of Formula III or IV can be in a liquid form (neat). For polyurethane foam preparation, in some modes of practice, the amine polyether polyol compound of Formula III or IV is in liquid form, have a molecular weight in the range of about 1000 Da to about 5000 Da, or both.

Compounds of Formula III or IV can optionally be described in terms of their solubility properties. For example, in some cases the amine polyether polyol compounds of Formula III or IV are soluble in a polar protic (e.g., water, methanol, ethanol, isopropanol, etc.) or polar aprotic solvent (tetrahydrofuran (THF), dimethyl sulfoxide (DMSO), acetonitrile, etc.).

Other aspects of the invention include compositions for making polyurethane foams, methods for making polyurethane foams, and polyurethane foams made using cyclic amine, amine alkoxylate, or amine polyether polyol components of the invention.

In some modes of practice, cyclic amine compounds of Formula I or II can be used in a composition to provide catalytic activity during the foam forming reaction. Included in the composition along with (a) the cyclic amine or amine alkoxylated compound are (b) a polyol compound, and (c) a polyisocyanate.

In other modes of practice, amine polyether polyol compounds of Formula III or IV can be used in a composition to provide both catalytic activity and a reactant source during the foam forming reaction. The amine polyether polyol compound can be used as the sole polyol material in the composition, or can be used along with one or more other polyol compounds. Therefore, included in the composition along with (a) the amine polyether polyols is (b) optionally, another polyol; and (c) a polyisocyanate.

Cyclic amine compounds of Formula I or II can be used in a composition at a desired concentration to provide catalytic activity during the foam forming reaction. Exemplary concentrations of the cyclic amine compound of Formula I or II are in the range of about 0.05 wt. % to about 1.5 wt. %, 0.1 wt. % to about 1 wt. %, or 0.2 wt. % to about 0.8 wt. %.

Exemplary polyols that can be used to produce polyurethane materials with the cyclic amines or amine alkoxylates of Formula I or II, or optionally with the amine polyether polyols of Formula III or IV, include those that are well known in the art. These include polyols described herein, commercially available polyols, and polyols described in the literature. General classes of polyols that can be used in the polyurethane foam forming composition include polyether polyols, polyester polyols, polyhydroxy-terminated acetal resins, hydroxyl-terminated amines, and polyamines (see, for example, U.S. Pat. No. 4,394,491). Other polyols classes include polyalkylene carbonate-based polyols and polyphosphate-based polyols. Copolymer polyols, some of which can be prepared by grafting methodologies, include styrene/acrylonitrile (SAN) copolymer polyols, polyisocyanate polyaddition (PIPA) polyols, and polyharnstoff dispersion (PHD) copolymer polyols. Copolymer polyols can include polymer segments other than the polyol portion to introduce desirable properties into the copolymer polyol, such as hardness. Exemplary polyols are also described in the Polyurethane Handbook (G. Oertel, Hanser publishers). The polyurethane foam forming composition can optionally include mixtures of one or more different polyol types, such as mixtures of two different polyols selected from polyol homopolymers and polyol copolymers.

Exemplary polyols included in the polyurethane foam-forming composition are alkylene oxide-based polyols prepared from polyol-generating monomers such as ethylene oxide, propylene oxide, butylene oxide, or combinations thereof. Alkylene oxide-based polyols can be made from monomer initiators with active hydrogen atoms, such as those having two or more hydroxyl or amine groups. In some polyol preparations, monomer initiators for making these polyols have from 2 to 8, or more specifically 2 to 6 active hydrogen atoms. Exemplary monomer initiators include organic dicarboxylic acids, such as succinic acid, adipic acid, phthalic acid and terephthalic acid and polyhydric alcohols, in particular dihydric to octahydric alcohols or dialkylene glycols, for example ethanediol, 1,2- and 1,3-propanediol, diethylene glycol, dipropylene glycol, 1,4-butanediol, 1,6-hexanediol, glycerol, trimethylolpropane, pentaerythritol, sorbitol and sucrose or blends thereof. These monomer initiators can be incorporated into the polyol product. Other initiators include linear and cyclic compounds containing an amine functionality such as N-methyldiethanolamine and triethanolamine The particular polyol, polyol mixture, and polyol amount used in the polyurethane foam forming composition can be chosen based on the factors such as the desired polyurethane foam properties and/or the particular end use of the foam product. Properties of the polyol such as molecular weight or hydroxyl number can be chosen to provide foam characteristics selected from: low density, high density foam, conventional, high resilient, hot molding, cold molding, flexible, and rigid, and desired combinations thereof. For many applications or foam properties, the hydroxyl number of the polyol is in the range of about 15 to about 800.

Compositions for the production of flexible polyurethane foams typically include a polyether polyol and/or a polyester polyol. The polyol generally has an average functionality ranging from 2 to 5, preferably 2 to 4, and an average hydroxyl number ranging from 20 to 100 mg KOH/g, preferably from 20 to 70 mgKOH/g (see, for example, U.S. Pat. No. 7,361,695).

For molded foam, the hydroxyl number of the base polyol can be in the range of about 20 to about 60 with ethylene oxide (EO) capping, and for slabstock foams the hydroxyl number can be in the range of about 25 to about 75 (see, for example, U.S. Pat. No. 7,361,695).

Polyurethane foam-forming compositions also include a polyisocyanate, such as an polyisocyanate selected from aliphatic, cycloaliphatic, arylaliphatic, and aromatic polyisocyanates. Aromatic polyisocyanates are preferred for the production of flexible foam.

Exemplary polyisocyanates include the 4,4'-, 2,4' and 2,2'-isomers of diphenylmethane diisocyante (MDI), blends thereof; polymeric and monomeric MDI blends; toluene-2, 4- and 2,6-diisocyanates (TDI), blends thereof; biuret modified TDI's, TDI/MDI blends; polymerized isocyanates, m- and p-phenylenediisocyanate, chlorophenylene-2,4-diisocyanate, diphenylene-4,4'-diisocyanate, 4,4'-diisocyanate-3,3'-dimethyldiphenyl, 3-methyldiphenyl-methane-4,4'-diisocyanate, diphenyletherdiisocyanate, 2,4,6-triisocyanatotoluene, and 2,4,4'-triisocyanatodiphenylether (see, for example, U.S. Pat. No. 7,361,695).

Examples of aliphatic polyisocyanates include ethylene diisocyanate, 1,6-hexamethylene diisocyanate, isophorone diisocyanate, cyclohexane 1,4-diisocyanate, 4,4'-dicyclohexylmethane diisocyanate, saturated analogues of the above mentioned aromatic isocyanates and mixtures thereof.

Isocyanate-terminated prepolymers are prepared by reacting an excess of polyisocyanate with polyols, including aminated polyols or imines/enamines thereof, or polyamines (see, for example, U.S. Pat. No. 7,361,695).

In some modes of preparing polyurethane foams, water is used as a blowing agent. Exemplary amounts of water are in the range of about 0.5 to about 10 parts by weight, or more specifically in the range of about 1 to about 6 parts by weight based on 100 parts by weight of the polyol. Generally, low density foams can be prepared using greater amounts of water, such as near the upper ends of these ranges, whereas high density foams can be prepared using lesser amounts of water, such as near the lower ends of these ranges. Carboxylic acids or salts can also be used as blowing agents.

Use of carbon dioxide, either as a gas or as a liquid, as auxiliary blowing agent, in addition to water can optionally be used. During foam formation, atmospheric pressure can be adjusted, frothing can be used, or combinations thereof, as described in U.S. Pat. No. 5,194,453 to vary foam density and comfort.

The composition can include other components in addition to the polyisocyanate and amine polyether polyol of Formulas III or IV, or in addition to the polyisocyanate, cyclic amine catalyst of Formulas I or II, and the polyol. These other components include, but are not limited to surfactants, preservatives, flame retardants, colorants, antioxidants, reinforcing agents, stabilizers, and fillers.

In making polyurethane foam, it is generally preferred to employ an amount of a surfactant to stabilize the foaming reaction mixture until it cures. In some formulations, the composition includes a liquid or solid organosilicone surfactant. Other surfactants include polyethylene glycol ethers of long-chain alcohols, tertiary amine or alkanolamine salts of long-chain alkyl acid sulfate esters, alkyl sulfonic esters and alkyl arylsulfonic acids. Surfactants can be used in amounts sufficient to stabilize the foaming reaction mixture against collapse and the formation of a desired cell structure. Exemplary amounts of surfactant are in the range of about 0.2 to about 3 parts of the surfactant per 100 parts by weight total polyol. Mixtures of surfactants can be used.

In some formulations, the composition can include an organometallic catalyst to promote the reaction of the polyol with the polyisocyanate. Exemplary organometallic catalysts include organomercury, organolead, organoferric and organotin catalysts. Exemplary tin catalysts include stannous chloride, tin salts of carboxylic acids such as dibutyltin di-laurate, as well as other organometallic compounds such as are disclosed in U.S. Pat. No. 2,846,408. A catalyst for the trimerization of polyisocyanates, resulting in a polyisocyanurate, such as an alkali metal alkoxide may also optionally be used in the foam forming compositions. Exemplary amounts of organometallic catalysts range from about 0.001 to about 1 percent in the composition.

Other components that can optionally be added to the foam forming composition include crosslinking agents and chain extenders. Exemplary crosslinking agents and chain extenders include low-molecular weight polyhydric alcohols such as ethylene glycol, diethylene glycol, 1,4-butanediol, and glycerin; low-molecular weight amine polyols such as diethanolamine and triethanolamine; diamines such as ethylenediamine and xylenediamine; and methylene-bis(o-chloroaniline). The use of such crosslinking agents or chain extenders is known in the art as disclosed in U.S. Pat. Nos. 4,863,979 and 4,963,399 and EP 549,120.

Foams produced using compounds of the invention can be used in applications known in the industry. For example, flexible foams find use in applications such as vehicle parts, such as seats, armrests, dashboards or instrument panels, sun visors, door linings, and noise insulation parts. Exemplary placement of the foams includes locations such as under the carpet or in other parts of the car interior or in the engine compartment. Foam of the invention can also be used in many domestic applications such as shoe soles, cloth interliners, appliance, furniture and bedding.

Processes for producing polyurethane foam products are well known in the art. In general components of the polyurethane-forming reaction mixture can be mixed together in any convenient manner, for example by using any of the mixing equipment described in the prior art such as in Polyurethane Handbook, by G. Oertel, Hanser publisher.

The polyurethane products can be produced continuously or discontinuously, by injection, pouring, spraying, casting, calendering, etc. Foams can be made under free rise or molded conditions, at atmospheric pressure, reduced or increased air pressure, with or without release agents, in-mold coating, or with any inserts or skin put in the mold. Flexible molded foams can be mono- or dual-hardness.

The polyurethane foams can optionally be described by one or more foam properties, including, but not limited to density, indentation force deflection (IFD), sag factor, recovery ratio, guide factor, compression load deflection (CLD), % compression set, tensile strength, elongation, and tear strength.

Density is weight per unit volume (weight/volume) and typically expressed as lbs/ft3 (pcf) or g/L. Exemplary densities are in the range of about 20 g/L to about 80 g/L, or more specifically in the range of about 25 g/L to about 32 g/L.

Compression force deflection (CFD), such as measured by the ISO 3386/1 standard, is a testing standard designed to measure the compression stress/strain (load divided by specimen surface area at a certain compression percentage) characteristic of foam. CFD is also a measure of firmness and is expressed in pounds per square inch (psi), at a given percentage deflection. Exemplary densities are in the range of about 20 g/L to about 80 g/L, or more specifically in the range of about 25 g/L to about 32 g/L.

Percent compression set (CS), such as measured by the ISO 1856 standard, is a measure of the permanent deformation of a foam after it has been compressed between two metal plates for a controlled time period and temperature condition. The standard conditions are 22 hours at 70° C. (158° F.). Exemplary compression set values are in the range of about 1 to about 20, or more specifically in the range of about 5 to about 7.

Tensile strength is a measure of the amount of force required to break an area of foam as it is pulled apart, and is generally expressed in pounds per square inch (psi). Foam compositions can be prepared to provide foam with a desired tensile strength, or a tensile strength within a desired range.

Elongation, such as measured by the ISO 1798 standard, is a measure of the extent to which the foam can be stretched before it breaks and is expressed as a percentage of its original length. Elongation is measured at the same time, as tensile strength is determined; therefore, the sample size is the same. Exemplary elongation values are in the range of about 50 to about 200, or more specifically in the range of about 110 to about 130.

Tear strength, such as measured by the ASTM D3574 standard, is a measure of the force required to continue a tear in foam after a split has been started and is expressed in pounds per linear inch (pli). Exemplary tear strengths are in the range of about 50 to about 350, or more specifically in the range of about 195 to about 230.

Example 1

BPEA-Polyol Preparation

Bis(2-(piperazin-1-yl)ethyl)amine (BPEA) was used as an initiator and alkoxylated with propylene oxide to a molecular weight of approximately 4700 Mw followed by a 17.5% ethylene oxide capping step.

Approximately 200 g of BPEA (829 mmol; 241.38 Da mw) was added to a reactor and heated to a temperature of ~105° C. Three mols of propylene oxide (174.24 g; 58.08 Da) was added to the reactor after 2 hours. Potassium hydroxide was added to the reaction product to a final concentration of 2500 ppm to react the rest of propylene oxide and ethylene oxide for the subsequent capping reaction. The final mixture was finished using a magnesium silicate filter process to remove the remaining catalyst. 600 ppm of Irganox 1076 are added to prevent oxidation and degradation.

Examples 2-6

Polyurethane Foam Preparation

Figure 2:
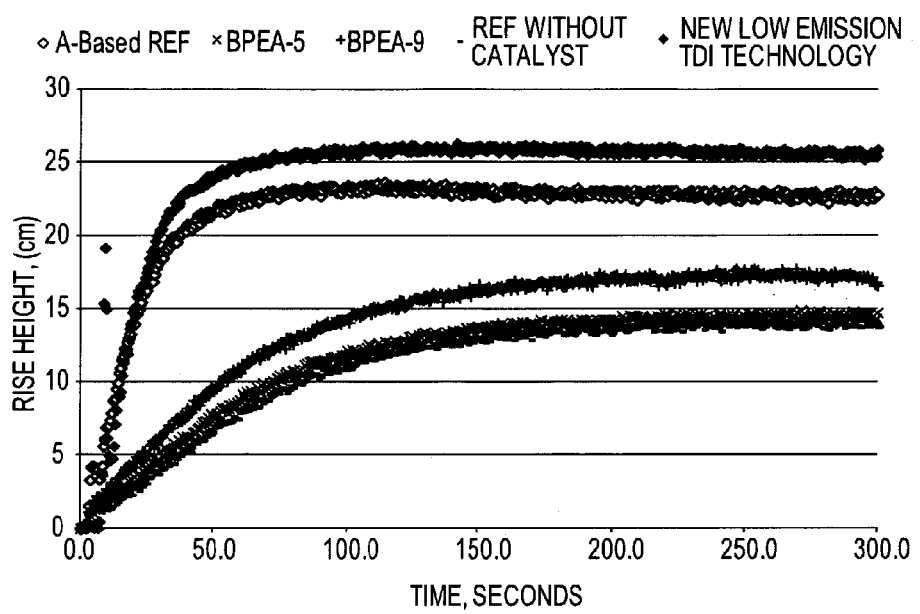
FIG. 2 is a graph showing the increase in height of polyurethane foam compositions over time.
Figure 3:
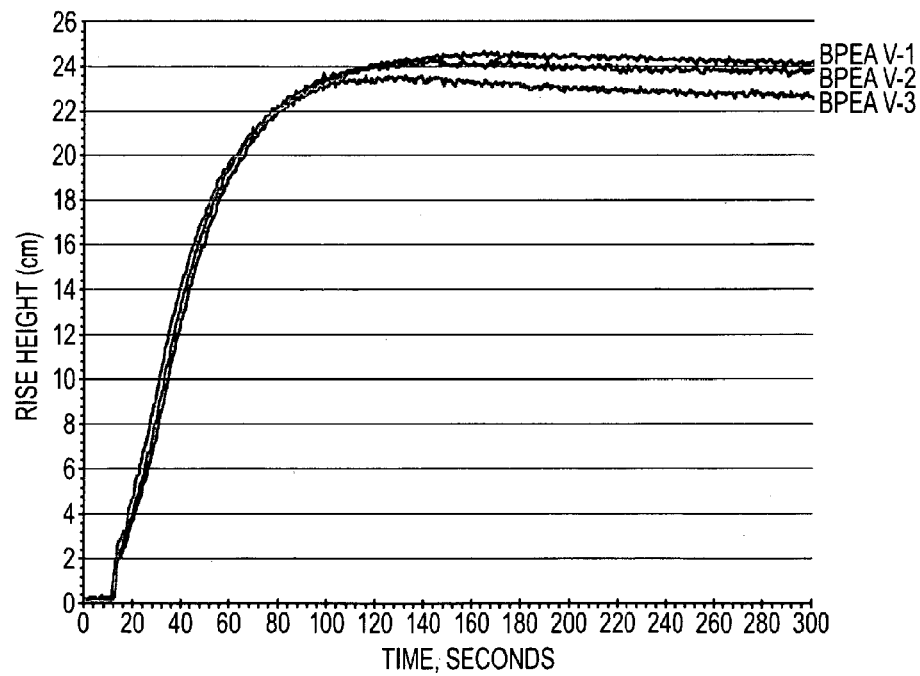
FIG. 3 is a graph showing the increase in height of polyurethane foam compositions over time.

All foams of Examples 2-6 were prepared by box foaming by blending approximately 500 g of the polyols with surfactant, catalyst, water of the type and amounts according to Table 1 and mixing between 2000-2500 RPM. The blend was then held for approximately 12 hours for adequate degassing. Subsequently, approximately 250 g of the polyol/catalyst/surfactant mixture was placed in a cup and stirred for 15 seconds and then the polyisocyanate was added to the cup while stirring for another 5-10 seconds depending on reactivity. The cup contents were poured into a plastic box to measure the free rise reactivity and rise height using FOAMAT equipment. Results are shown in FIGS. 1 and 2.

TABLE 1

| | 2 | 3 | 4 | 5 | 6 |
|---|---|---|---|---|---|
| Isocyanate-Reactive Component (Parts by wt.) | | | | | |
| Polyol - A | 34.38 | 34.35 | 34.1 | 34.8 | 34.5 |
| Polyol - B | 60 | 60 | 60 | 60 | 40.3 |
| Catalyst - A | | 0.35 | 0.7 | | |
| Catalyst - B | 0.35 | | | | |
| Catalyst - C | 0.07 | | | | |
| DEOA | 0.7 | 0.7 | 0.7 | 0.7 | 0.7 |
| Glycerine | 0.5 | 0.5 | 0.5 | 0.5 | 0.5 |
| Surfactant | 0.7 | 0.7 | 0.7 | 0.7 | 0.7 |
| Water | 3.3 | 3.3 | 3.3 | 3.3 | 3.3 |
| Isocyanate | | | | | |
| Isocyanate (TDI) | 100 | 100 | 100 | 100 | 100 |

Polyol A: DNC 701.01
Polyol B: Specflex NC632: Specialty Capped Polyol with high MW, functionality and primary hydroxyl content.
Catalyst - A: BPEA
Catalyst - B: DABCO 33LV: Contains 33% triethylene diamine and 67% dipropylene glycol (Air Products)
Catalyst - C: NIAX A-1: Contains 70 percent bis(2-dimethylaminoethyl) ether, diluted with 30 weight percent of dipropylene glycol (Momentive)
DEOA: diethanolamine
Surfactant: Tegostab B8736 LF2: silicone surfactant (Evonik)
Voranate T-80: TDI 80/20 (Dow)

Examples 7-9

Polyurethane Foam Preparation

Foams of Examples 7-9 were prepared according to the method described in Examples 2-6 using reagents in amounts according to Table 2. Various foam properties were tested and are shown in Table 3.

TABLE 2

| | 7 | 8 | 9 |
|---|---|---|---|
| Isocyanate-Reactive Component (Parts by wt.) | | | |
| Polyol - C | 34.38 | 34.1 | 33.75 |
| Polyol - B | 60 | 60 | 60 |
| Catalyst - A | | 0.35 | 0.7 |
| Catalyst - B | 0.35 | 0.35 | 0.35 |
| Catalyst - C | 0.07 | | |
| DEOA | 0.7 | 0.7 | 0.7 |

TABLE 2-continued

| | 7 | 8 | 9 |
|---|---|---|---|
| Glycerine | 0.5 | 0.5 | 0.5 |
| Surfactant | 0.7 | 0.7 | 0.7 |
| Water | 3.3 | 3.3 | 3.3 |
| Isocyanate | | | |
| Isocyanate (TDI) | 100 | 100 | 100 |

Polyol C: Specflex NC700: copolymer polyol formed by in situ polymerization of styrene and acrylonitrile
Polyol B: Specflex NC632: Specialty Capped Polyol with high MW, functionality and primary hydroxyl content.
Catalyst - A: BPEA
Catalyst - B: DABCO 33LV: Contains 33% triethylene diamine and 67% dipropylene glycol (Air Products)
Catalyst - C: NIAX A-1: Contains 70 percent bis(2-dimethylaminoethyl) ether, diluted with 30 weight percent of dipropylene glycol (Momentive)
DEOA: diethanolamine
Surfactant: Tegostab B8736 LF2: silicone surfactant (Evonik)
Voranate T-80: TDI 80/20 (Dow)

TABLE 3

| | 7 | 8 | 9 |
|---|---|---|---|
| Index | 100 | 100 | 100 |
| CFD, Iso 3386 | | | |
| F40%, kPa | 2.12 | 2.75 | 3.01 |
| Density, g/l | 26.41 | 28.81 | 30.11 |
| Elongation, Iso 1798 | 125 | 124.8 | 115.2 |
| Tear, ASTM D3574 | 209.3 | 227.5 | 198.8 |
| Resilience, D3574 | 62 | 62 | 61 |
| CS, ISO 1856 | 6.8 | 5.6 | 5.3 |
| Wet CS, Renault 1637W, spec <20 (±2) | 24 | 17 | 15 |
| Elongation, ageing 200 h 90° C., VW, PV 3410 | 134 | 135 | 124 |
| % Elongation change, VW spec >80% | 93 | 92 | 93 |

What is claimed is:
1. A composition comprising a reaction product derived from reactants comprising, or a reaction composition having reactants comprising:
 (a) a cyclic amine or amine alkoxylate of Formula I:

[Chemical structure of Formula I]

or of Formula II

[Chemical structure of Formula II]

where, in Formula I or II, $R^1$-$R^7$ and $R^{1'}$-$R^{7'}$ are independently selected from the group consisting of hydrogen and hydrocarbyl groups; x and x' are independently 0 or an integer in the range of 1-10, and if x or x' is greater than 1, then $R^1$ and $R^{1'}$ are the same or different; and Z, Z', and Z" are independently selected from the group consisting of hydrogen —$CH_2CH_2OH$, —$CH_2CH(CH_3)OH$, —$CH(CH_3)CH_2OH$, —$CH_2CH(CH_2CH_3)OH$, or —$CH(CH_2CH_3)CH_2OH$; and (b) a polyol-generating monomer.

2. The composition of claim 1 wherein the polyol-generating monomer is selected from the group consisting of epoxides and haloalcohols, or the group consisting of ethylene oxide, propylene oxide, and butylene oxide.

3. The composition of claim 1, where in Formula I, II, III, or IV, x and x' are 0.

4. The composition of claim 1 where in Formula I or II, R, $R^1$-$R^7$, and $R^{1'}$-$R^{7'}$ are hydrogen.

5. The composition of claim 1 wherein the cyclic amine of Formula I is bis(2-piperazin-1-ylethyl)amine; the cyclic amine of the Formula II is 2-(4-(2-(piperazin-1-yl)ethyl)piperazin-1-yl)ethanamine; the amine alkoxylate of Formula I is 2,2'-(4,4'-(((2-hydroxyethyl)azanediyl)bis(ethane-2,1-diyl))bis(piperazine-4,1-diyl))diethanol, 1,1'-(4,4'-(((2-hydroxypropyl)azanediyl)bis(ethane-2,1-diyl))bis(piperazine-4,1-diyl))bis(propan-2-ol), or 1,1'-(4,4'-(((2-hydroxybutyl)azanediyl)bis(ethane-2,1-diyl))bis(piperazine-4,1-diyl))bis(butan-2-ol); or the amine alkoxylate of Formula II is 2,2'-((2-(4-(2-(4-(2-hydroxyethyl)piperazin-1-yl)ethyl)piperazin-1-yl)ethyl)azanediyl)diethanol, 1,1'-((2-(4-(2-(4-(2-hydroxypropyl)piperazin-1-yl)ethyl)piperazin-1-yl)ethyl)azanediyl)bis(propan-2-ol), or 1,1'-((2-(4-(2-(4-(2-hydroxybutyl)piperazin-1-yl)ethyl)piperazin-1-yl)ethyl)azanediyl)bis(butan-2-ol).

6. An amine polyether polyol of Formula III:

7. The amine polyether polyol of claim 6, where in Formula I, II, III, or IV, x and x' are 0.

8. The amine polyether polyol of claim 6, where in Formula III, or IV, R, $R^1$-$R^7$, $R^{10}$, $R^{1'}$-$R^{7'}$, and $R^{10'}$ are hydrogen.

9. The amine polyether polyol of claim 6 where, in Formula III or IV, y, y', and y" are independently integers in the range of 1 to 250; compounds of Formula III or IV have a hydroxyl number in the range of 401.6 mg/g to 24 mg/g; or compounds of Formula III or IV have a molecular weight in the range of 296 Da to 8000 Da.

10. The amine polyether polyol of claim 9 where, in Formula III or IV, y, y', and y" are independently integers in the range of 10 to 100.

11. A method for preparing an amine polyether polyol comprising a step of reacting a cyclic amine or amine alkoxylate of Formula I or II according to claim 1 with a polyol-generating monomer.

12. A polyurethane foam derived from a composition comprising, or a composition having components comprising:

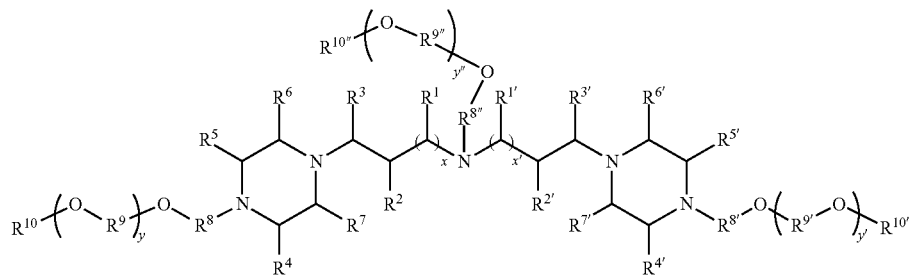

or of Formula IV:

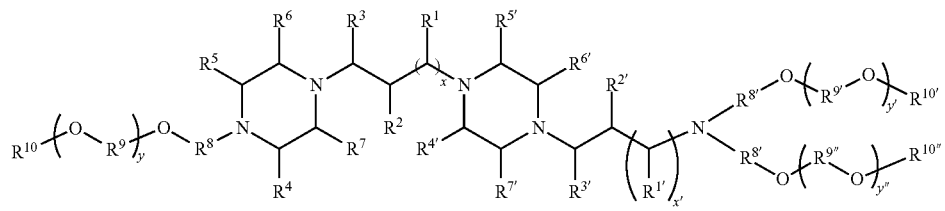

where, in Formula III or IV, $R^1$-$R^7$, $R^{10}$, $R^{1'}$-$R^{7'}$, $R^{10'}$ and $R^{10"}$ are independently selected from the group consisting of hydrogen and hydrocarbyl groups; x and x' are independently 0 or an integer in the range of 1-10, and if x or x' is greater than 1, then $R^1$ and $R^{1'}$ are the same or different; $R^8$, $R^{8'}$, $R^{8"}$, $R^9$, $R^{9'}$, and $R^{9"}$ are independently selected from —$CH_2CH_2$—, —$CH_2CH(CH_3)$—, —$CH(CH_3)CH_2$—, —$CH_2CH(CH_2CH_3)$—, and —$CH(CH_2CH_3)CH_2$—, and y, y', and y" are independently 0 or an integer in the range of 1 to 250, provided the sum of y, y', and y" is 1 or greater.

(a) a cyclic amine or amine alkoxylate of Formula I:

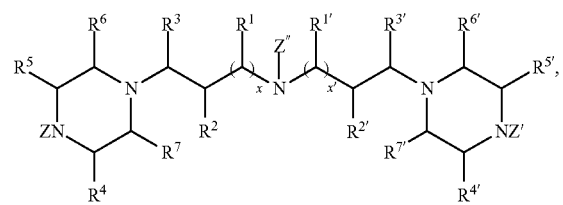

or of Formula II

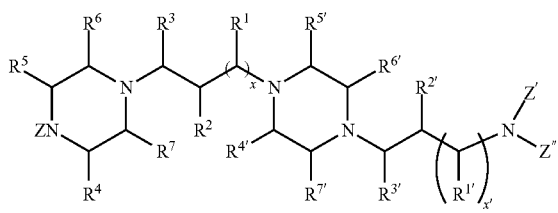

where, in Formula I or II, $R^1$-$R^7$ and $R^{1'}$-$R^{7'}$ are independently selected from the group consisting of hydrogen and hydrocarbyl groups; x and x' are independently 0 or an integer in the range of 1-10, and if x or x' is greater than 1, then $R^1$ and $R^{1'}$ are the same or different; and Z, Z', and Z" are independently selected from the group consisting of hydrogen —$CH_2CH_2OH$, —$CH_2CH(CH_3)OH$, —$CH(CH_3)CH_2OH$, —$CH_2CH(CH_2CH_3)OH$, or —$CH(CH_2CH_3)CH_2OH$;

(b) a polyol, and
(c) a polyisocyanate;
or, from reactants comprising
(a) an amine polyether polyol of Formula III:

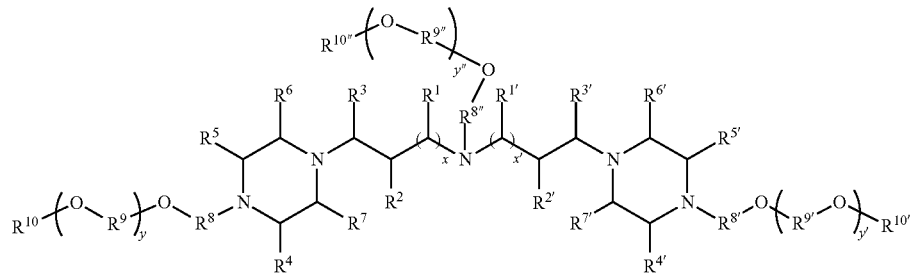

or of Formula IV:

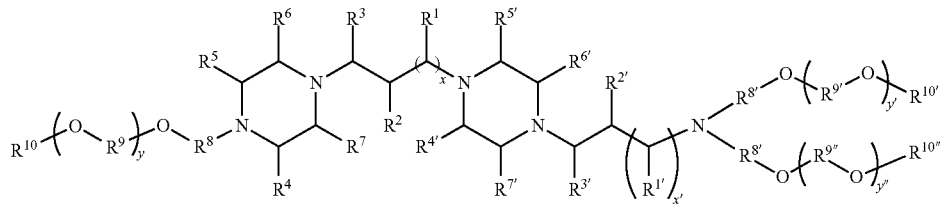

where, in Formula III or IV, $R^1$-$R^7$, $R^{10}$, $R^{1'}$-$R^{7'}$, $R^{10'}$ and $R^{10''}$ are independently selected from the group consisting of hydrogen and hydrocarbyl groups; x and x' are independently 0 or an integer in the range of 1-10, and if x or x' is greater than 1, then $R^1$ and $R^{1'}$ are the same or different; $R^8$, $R^{8'}$, $R^{8''}R^9$, $R^{9'}$, and $R^{9''}$ are independently selected from —$CH_2CH_2$—, —$CH_2CH(CH_3)$—, —$CH(CH_3)CH_2$—, —$CH_2CH(CH_2CH_3)$—, —$CH(CH_2CH_3)CH_2$—, and y, y', and y" are independently 0 or an integer in the range of 1 to 250, provided the sum of y, y', and y" is 1 or greater;

(b) optionally, a polyol; and
(c) a polyisocyanate.

13. The polyurethane foam of claim 12 derived from reactants further comprising (d) an amine catalyst that is different than the (a) cyclic amine or amine alkoxylate of Formula I or II or the (a) amine polyether polyol of Formula III or IV.

14. A method for preparing a polyurethane foam comprising a step of reacting a polyol and a polyisocyanate in the presence of a cyclic amine or amine alkoxylate of Formula I or II according to claim 12; or a step of reacting an amine polyether polyol of Formula III or IV according to claim 12 with a polyisocyanate, optionally in the presence of a polyol.

15. The composition of claim 1, where, in the reactants, the ratio of the (a) a cyclic amine or amine alkoxylate of Formula I or II to the (b) polyol-generating monomer is in the range of 1:30 to 1:600 (mol:mol), respectively.

16. The composition of claim 1, where, in the reactants, the ratio of the (a) a cyclic amine or amine alkoxylate of Formula I or II to the (b) polyol-generating monomer is in the range of 1:75 to 1:300 (mol:mol), respectively.

* * * * *

UNITED STATES PATENT AND TRADEMARK OFFICE
CERTIFICATE OF CORRECTION

PATENT NO. : 9,611,351 B2
APPLICATION NO. : 14/369626
DATED : April 4, 2017
INVENTOR(S) : Stephen W. King et al.

Page 1 of 1

It is certified that error appears in the above-identified patent and that said Letters Patent is hereby corrected as shown below:

On the Title Page

(72) Inventors:
"Jean-Paul Massy" should be --Jean-Paul Masy--

Signed and Sealed this
Twelfth Day of June, 2018

Andrei Iancu
*Director of the United States Patent and Trademark Office*